United States Patent
Ahmed (12)

(10) Patent No.: US 6,281,248 B1
(45) Date of Patent: Aug. 28, 2001

(54) COMPOSITION FOR TREATING ASTHMA

(76) Inventor: Magda Abdel Fattah Ahmed, 1035-45ST, Brooklyn, NY (US) 11219

( * ) Notice: Subject to any disclaimer, the term of this patent is extended or adjusted under 35 U.S.C. 154(b) by 0 days.

(21) Appl. No.: 09/505,747

(22) Filed: Feb. 16, 2000

(51) Int. Cl.$^7$ ................................................. A61K 31/135
(52) U.S. Cl. ............................................................ 514/657
(58) Field of Search ............................................. 514/657

(56) References Cited

U.S. PATENT DOCUMENTS

| | | |
|---|---|---|
| 4,089,959 | 5/1978 | Diamond . |
| 4,837,203 | 6/1989 | Adcock . |
| 5,179,089 | 1/1993 | Tackacs et al. . |
| 5,705,505 | 1/1998 | Shenvi et al. . |

OTHER PUBLICATIONS

Carson, Am J. Forensic Med Pathol. 21 (3) 273–5 abstract, 2000.*

* cited by examiner

*Primary Examiner*—Rebecca Cook

(57) ABSTRACT

A method of treating asthma that includes the step of controlling the asthma by ingesting a composition which includes a selective serotonin reuptake inhibitor that is sertraline hydrochloride. Chronic administration of the sertraline thereof downregulates brain norepinephrine receptors. The increased output of the brain norepinephrine receptors increases the dilation of the bronchi. Sertraline has no significant affinity for adrenergic (alpha$_1$, alpha$_2$, beta), cholinergic, GABA, dopaminergic, histaminergic, serotonergic (5HT$_{1A}$, 5HT$_{1B}$, 5HT$_2$), or benzodiazepine receptors. Antagonism of such receptors has been hypothesized to be associated with various adverse anticholinergic, sedative, and cardiovascular effects.

2 Claims, 1 Drawing Sheet

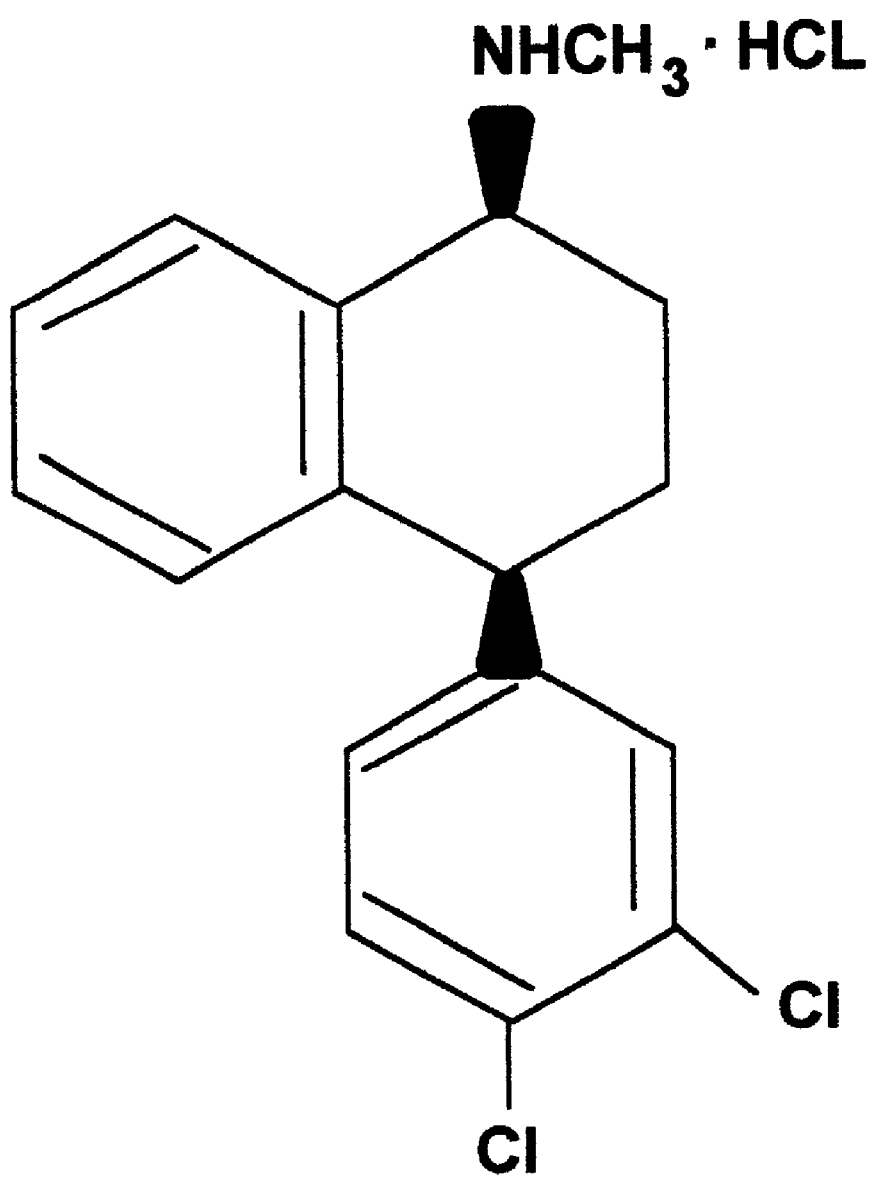

COMPOSITION FOR TREATING ASTHMA

BACKGROUND OF THE INVENTION

1. Field of the Invention

The present invention relates to a composition. More particularly, the present invention relates to a composition for treating asthma.

2. Description of the Prior Art

The frequency of occurrence of allergic diseases, particularly bronchial asthma is continuously increasing. Social-economical and environmental conditions, enhancement of affectivity of the diagnosis, and the lack of an adequate, really healing therapy provide background of this increase. Despite for or partially even due to the elevated drug consumption, the mortality ratio also shows a rising tendency.

Bronchial asthma is characterized by bronchospasm caused by contraction of the bronchial smooth muscle, increased secretion of mucus from the bronchi, and edema of the respiratory mucosa.

While the etiology of asthma is not completely known, it is believed to involve an allergic reaction. Allergic reactions occur in sensitized individuals who are exposed to the antigen to which they are sensitized. The antigen provokes the release in the body of certain chemicals (allergic mediators) which in turn produce the allergic symptoms. Allergic reactions can also produce effects in organs other than the bronchi, particularly the skin, the eyes, and nasal mucosa, and include such diseases as allergic rhinitis and urticaria.

Acute asthmatic bronchospasm has been treated with drugs which relax bronchial smooth muscle. Sympathomimetic drugs, such as epinephrine, isoproterenol, and terbutaline and xanthine drugs, such as theophylline and its salts (aminophylline, etc.) have been used for this purpose. Drugs, such as cromolyn which inhibit the release of allergic mediators, have been used prophylactically to treat bronchial asthma. Corticosteroid drugs have also been used to treat bronchial asthma and other allergy diseases.

Many of the drugs used hitherto have short comings which make them less than ideal for treatment of asthma and other bronchspastic and allergic diseases. For example, epinephrine and isoproterenol relieve the symptoms of asthma for only a relatively short period of time and are ineffective orally. Theophylline has limited efficacy and produces cardiac and gastrointestinal side effects. Cromolyn sodium is only effective by inhalation or injection and is ineffective by oral administration. The corticosteroid drugs have serious side effects which limit their chronic use.

Numerous innovations for asthma treatments have been provided in the prior art that will be described. Even though these innovations may be suitable for the specific individual purposes to which they address, however, they differ from the present invention in that they only relieve the symptoms of asthma for a relatively short period of time, are ineffective orally, have limited efficacy, produce cardiac and gastrointestinal side effects, are only effective by inhalation or injection and are ineffective by oral administration, and have serious side effects which limit their chronic use.

FOR EXAMPLE, U.S. Pat. No. 4,089,059 to Diamond teaches prolonged bronchodilation and prolonged inhibition of allergic mediator release in mammals are produced by administering an effective amount of a substituted xanthine compound having the formula: ##STR1## wherein: $R_1$=methyl $R_3$=$c_4$ –$c_7$ alkyl, $C_4$–$C_7$ cycloalkylalkyl $C_4$–$C_7$ alkenyl, $C_4$–$C_7$ alkynyl, or $C_4$–$C_7$ cycloalkyl $R_8$=$c_1$–$c_2$ alkyl. Those compounds are useful in the treatment of bronchial asthma and other bronchospastic and allergic diseases. The bronchodilator and antiallergy agents may be administered in the form of tablets, capsules, aerosols, solutions, suspensions or suppositories.

ANOTHER EXAMPLE, U.S. Pat. No. 4,837,203 to Adcock et al. teaches peptides of the formula X--Tyr--$X^2$--Gly--Phe(4$NO_2$)--Pro--$NH_2$ wherein X is hydrogen or an amidino group and $X^2$ is D-S-methylmethionyl or D-arginyl, together with their pharmacologically acceptable salts, which have been described as exhibiting analgesic, antidiarrheal and antitussive activity, are effective in reversing neuronally-mediated bronchoconstriction in mammals. The said compounds have application in the palliation of conditions characterized by such a state, in particular asthma in human beings.

STILL ANOTHER EXAMPLE, U.S. Pat. No. 5,179,089 to Takacs et al. teaches compounds of the general formula (I), ##STR1## wherein R means hydrogen or a straight or branched chain $C_{1-6}$ alkoxy group; $P^1$ stands for hydrogen or a straight or branched chain $C_{1-6}$ alkyl group; $R^2$ represents hydrogen or a straight or branched chain $C_{1-6}$ alkyl group; $R^3$ means hydrogen, a straight or branched chain $C_{1-6}$ alkyl group optionally substituted by one or two hydroxyl and/or one or two straight or branched chain $C_{1-4}$ alkoxy group(s); or a $C_{4-7}$ cycloalkyl group; $R^4$ stands for hydrogen or a straight or branched chain $C_{1-6}$ alkyl group optionally substituted by one or two hydroxyl and/or one or two straight or branched chain $C_{1-4}$ alkoxy group(s); or a $C_{4-7}$ cycloalkyl group; or $R^3$ and $R^4$ together with the nitrogen atom, to which they are attached form a 4 to 8-membered cyclic group of formula ##STR2## optionally substituted by one or two straight or branched chain $C_{1-4}$ alkoxy and/or one or two straight or branched chain $C_{1-4}$ alkyl group(s), where optionally an oxygen or sulfur atom or an N-$R^5$ group may be substituted for a ring carbon atom, where $R^5$ means hydrogen or a straight or branched chain $C_{1-6}$ aliphatic alkyl group, the 4- to 8-membered cycle optionally being condensed with a benzene ring; $R^6$ stands for hydrogen or a $C_{1-10}$ acyl group and the salts and hydrates thereof as well as pharmaceutical compositions containing these compounds. The compounds of the invention antagonize the effects of constrictive mediators, e.g. histamine, acetylcholine or serotonin; they show an antiallergic action and possess an antiinflammatory effect. Thus, these compounds can therapeutically be used as bronchodilators as well as antiallergic or antiinflammatory drugs, particularly in the treatment of bronchial asthma.

STILL ANOTHER EXAMPLE, U.S. Pat. No. 5,705,505 to Shenvi et al. teaches compounds of formula I ##STR1## wherein $Q^1$, $Q^2$, $Q^3$, and $Q^4$ have any of the meanings given in the specification, their N-oxides, and their pharmaceutically acceptable salts are nonpeptide antagonists of neurokinin A and useful for the treatment of asthma, etc. Also disclosed are pharmaceutical compositions, processes for preparing the compounds of formula I and intermediates.

It is apparent that numerous innovations for asthma treatments have been provided in the prior art that are adapted to be used. Furthermore, even though these innovations may be suitable for the specific individual purposes to which they address, however, they would not be suitable for the purposes of the present invention which is to relieve the symptoms of asthma for a long period of time, is effective orally, has unlimited efficacy, produces no cardiac and gastrointestinal side effects, is effective by oral administration, and has no serious side effects which limit its chronic use.

SUMMARY OF THE INVENTION

ACCORDINGLY, AN OBJECT of the present invention is to provide a composition for treating asthma that avoids the disadvantages of the prior art.

ANOTHER OBJECT of the present invention is to provide a composition for treating asthma that is simple to use.

BRIEFLY STATED, STILL ANOTHER OBJECT of the present invention is to provide a method of treating asthma that includes the step of controlling the asthma by ingesting a composition which includes a selective serotonin reuptake inhibitor that is sertraline hydrochloride. Chronic administration of the sertraline thereof downregulates brain norepinephrine receptors. The increased output of the brain norepinephrine receptors increases the dilation of the bronchi. Sertraline has no significant affinity for adrenergic (alpha$_1$, alpha$_2$, beta), cholinergic, GABA, dopaminergic, histaminergic, serotonergic (5HT$_{1A}$, 5HT$_{1B}$, 5HT$_2$), or benzodiazepine receptors. Antagonism of such receptors has been hypothesized to be associated with various adverse anticholinergic, sedative, and cardiovascular effects.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The sole FIGURE of the drawing is the structural formula of the present invention.

DETAILED DESCRIPTION OF THE PREFERRED EMBODIMENT

Description

The present invention is a selective serotonin reuptake inhibitor (SSRI), sertraline hydrochloride, for oral administration.

The present invention has a molecular weight of 342.7.

The present invention has a chemical name of:

(1S-cis)-4-(3,4-dichlorophenyl)-1,2,3,4-tetrahydro-N-methyl-1-naphthalenamine hydrochloride The present invention has an empirical formula of:

$C_{17}H_{17}NCl_2 \cdot HCL$

The present invention has a structural formula that is represented by the sole FIGURE.

The present invention is a white crystalline powder that is slightly soluble in water and isopropyl alcohol, and sparing soluble in ethanol.

The present invention comprises:
1) 25, 50, and 100 mg. of sertraline.
2) Dibasic calcium phosphate dihydrate.
3) Hydroxypropyl cellulose.
4) Hydroxypropyl methylcelluse.
5) Magnesium stearate.
6) Microcrystalline cellulose.
7) Polyethylene glycol.
8) Polysorbate 80.
9) Sodium starch glycolate.
10) Titanium dioxide.

Clinical Pharmacology

Pharmacodynamics

The mechanism of action of sertraline is presumed to be linked to its inhibition os CNS neuronal uptake of serotonin (5HT).

Even though applicant does not understand for sure the theory explaining how the present invention achieves its aim, is no reason for not granting patentability, as was decided In re *Bowden,* 183 F.2d 115, 119, 86 USPQ 419 (CCPA 1950), where the Court held:

"Under the patent will be issued to an inventor although he may not understand the principle upon which his invention works." [Emphasis added]

In this same regard, the Examiner's attention is respectfully directed to the decisions in *Diamond Rubber Co. v. Consolidated Rubber Tire Co.,* 220 U.S. 428, 55 L.Ed. 527, 31 S.Ct. 444 (1911); and *Cf. DeForest Radio co. v. General Elec. Co.,* 283 U.S. 664, 668, 75 L.Ed. 1339, 51 S.Ct. 563, 7 USPQ 67 (1931).

EXAMPLE I

Studies at clinically relevant doses in man have demonstrated that sertraline blocks the uptake of serotonin into human platelets.

EXAMPLE II

In vitro studies in animals also suggest that sertraline is a potent and selective inhibitor neuronal serctonin reuptake and has only very weak effects on norepinephrine and dopamine neuronal reuptake.

EXAMPLE III

In vitro studies have shown that sertraline has no significant affinity for adrenergic (alpha$_1$, alpha$_2$, beta), cholinergic, GABA, dopaminergic, histaminergic, serotonergic (5HT$_{1A}$, 5HT$_{1B}$, 5HT$_2$), or benzodiazepine receptors, and does not inhibit monoamine oxidase; antagonism of such receptors has been hypothesized to be associated with various adverse anticholinergic, sedative, and cardiovascular effects.

EXAMPLE IV

The chronic administration of sertraline was found in animals to downregulate brain norepinephrine receptors increasing dilation of the bronchi.

Pharmacokinetics

Systemic Bioavailability

EXAMPLE V

In man, following oral once-daily dosing over the range of 50 to 200 mg. for 14 days, mean peak plasma concentrations ($C_{max}$) of sertraline occurred between 4.5 to 8.4 hours post-dosing.

EXAMPLE VI

Linear dose-proportional pharmacokinetics were demonstrated on a single dose study in which $C_{max}$ and area under plasma concentration time curve (AUC) of sertraline were proportional to dose over a range of 50 to 200 mg. Consistent with the terminal elimination half-life[1], there is an approximately two-fold accumulation, compare to a single dose, of sertraline with repeated dosing over a 50 to 200 mg. dose range. The single dose bioavailability of sertraline tablets is approximately equal to an equivalent dose of solution.

[1] The average termination half-life of plasma sertraline is about 26 hours. Based on this pharmacokinetics parameter, steady-state sertraline plasma levels should be achieved after approximately one week of once-daily dosing.

EXAMPLE VII

The effects of food on the bioavailability of sertraline were studied in subjects administered a single dose with and without food. AUC was slightly increased when drug was administered with food, but the $C_{max}$ was 25% greater, while the time to reach peak plasma concentration decreased from 8 hours post-dosing to 5.5 hours.

Pharmacokinetics

Metabolism

Sertraline undergoes extensive first pass metabolism. The principal initial pathway of metabolism for sertraline is N-demethylation. N-demethylsertraline has a plasma terminal elimination half-life of 62 to 104 hours.

EXAMPLE VIII

Both in vitro biochemical and in vivo pharmacological testing have shown N-demethylsertraline to be substantially less active than sertraline. Both sertraline and N-demethylsertraline undergo oxidative deamination and subsequent reduction, hydroxylation, and glucuronide conjugation.

EXAMPLE IX

In a study of radiolabeled sertraline involving two healthy male subjects, sertraline accounted for less than 5% of the plasma radioactivity. About 40–45% of the administered radioactivity was recovered in urine in 9 days. Unchanged sertraline was not detectable in the urine. For the same period, about 40–45% of the administered radioactivity was accounted for in feces, including 12–14% unchanged sertraline.

EXAMPLE X

Desmethylsertraline exhibits time-related, dose dependent increases in AUC (0–24 hour), $C_{max}$, and $C_{min}$, with about a 5–9 fold increase in these pharmacokinetics parameters between day 1 and day 14.

Pharmacokinetics

Protein Binding

EXAMPLE XI

In vitro protein binding studies performed with radiolabeled $^3$H-sertraline showed that sertraline is highly bound to serum proteins (98%) in the range 20 to 500 ng/mL. At up to 300 and 200 ng/mL concentrations, respectively, however, sertraline and desmethylsertraline did not alter the plasma protein binding of two other highly protein bound drugs viz., warfarin and propranolol.

Pharmacokinetics

Pediatric Pharmacokinetics

EXAMPLE XII

Sertraline pharmacokinetics were evaluated in a group of 61 pediatric patients (29 aged 6–12, 32 aged 13–17 years). Patients included both males (n=28) and females (n=33). During 42 days of chronic sertraline dosing, sertraline was titrated up to 200 mg/day and maintained at that does for a minimum of 11 days. On the final day of sertraline 200 mg/day, the 6–12 year old group exhibited a mean sertraline AUC (0–24 hr) of 3107 ng-hr/ml, mean $C_{max}$ of 165 ng/mL, and mean half-life of 26.2 hr. The 13=17 year old group exhibited a mean sertraline AUC (0–24 hr) of 2296 ng-hr/mL, mean $C_{max}$ of 123 ng/mL, and mean half-life of 27.8 hr. Higher plasma levels in the 6–12 year old group were largely attributable to patients with lower body weights. No gender associated differences were observed.

EXAMPLE XIII

A group of 22 separately studied adults between 18 and 45 years of age (11 male, 11 female) received 30 days of 200 mg/day sertraline and exhibited a mean sertraline AUC (0–24 hr) of 2570 ng-hr/mL, mean $C_{max}$ of 142 ng/mL, and mean half-life of 27.2 hr. Relative to the adults, both the 6–12 year olds and the 13–17 year olds showed about 22% lower AUC (0–24 hr) and $C_{max}$ values when plasma concentration was adjusted for weight.

These data suggest that pediatric patients metabolize sertraline with slightly greater efficiency than adults. Nevertheless, lower doses may be advisable for pediatric patients given their lower body weights, especially in very young patients to avoid excessive plasma levels.

Pharmacokinetics

Age

EXAMPLE XIV

Sertraline plasma clearance in a group of 16 (8 male, 8 female) elderly patients treated for 14 days at a dose of 100 mg/day was approximately 40% lower than a similarly studied group of younger (25 to 32 y.o.) individuals. Steady-state, therefore, should be achieved after 2 to 3 weeks in older patients. The same study showed a decreased clearance of desmethlsertraline in older males, but not in older females.

Contraindications

Concomitant use of the sertraline hydrochloride in patients taking monoamine oxidase inhibitors (MAOIs) is contraindicated.

Precautions

General

Use In Patients With Concomitant Illness

EXAMPLE XV

Electrocardiograms of 774 patients who received sertraline hydrochloride in double-blind trials were evaluated and the data indicate that the sertraline hydrochloride is not associated with the development of significant ECG abnormalities.

Precautions

Drug Interactions

Drugs Metabolized By P450 3A4

EXAMPLE XVI

In two separate in vivo interaction studies, sertraline was co-administered with cytosome P450 3A4 substrates, terfenadine, or carmazepine.

Precautions

Drug Interactions

Atenolol

EXAMPLE XVII

When 100 mg of sertraline hydrochloride was administered to 10 healthy male subjects had no effect on the beta-adrenergic blocking ability of atenolol.

Precautions

Drug Interactions

Digoxin

EXAMPLE XVIII

In a placebo-controlled trial in normal volunteers, administration of sertraline hydrochloride for 17 days (including 200 mg/day for the last 10 days) did not change serum digoxin levels or digoxin renal clearance.

Precautions

Drug Interactions

Mutagenesis

EXAMPLE XIX

Sertraline had no genotoxic effects, with or without metabolic activation, based on the following assays: bacterial mutation assay; mouse lymphoma mutation assay; and tests for cytogenetic aberrations in vivo mouse boric marrow arid in vitro in human lymphocytes.

Conclusion

While the invention has been illustrated and described as embodied in a composition for treating asthma, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A method of treating asthma in a subject in need thereof, comprising the step of administering to the subject an effective amount of sertraline hydrochloride.

2. The method as defined in claim 1, wherein said step of administering to the subject an effective amount of sertraline hydrochloride comprises administering to the subject an effective amount of sertraline hydrochloride in tablet form taken orally.

* * * * *